March 22, 1966 C. J. HAUCK Plant Pat. 2,614
LILAC PLANT
Filed Nov. 8, 1962
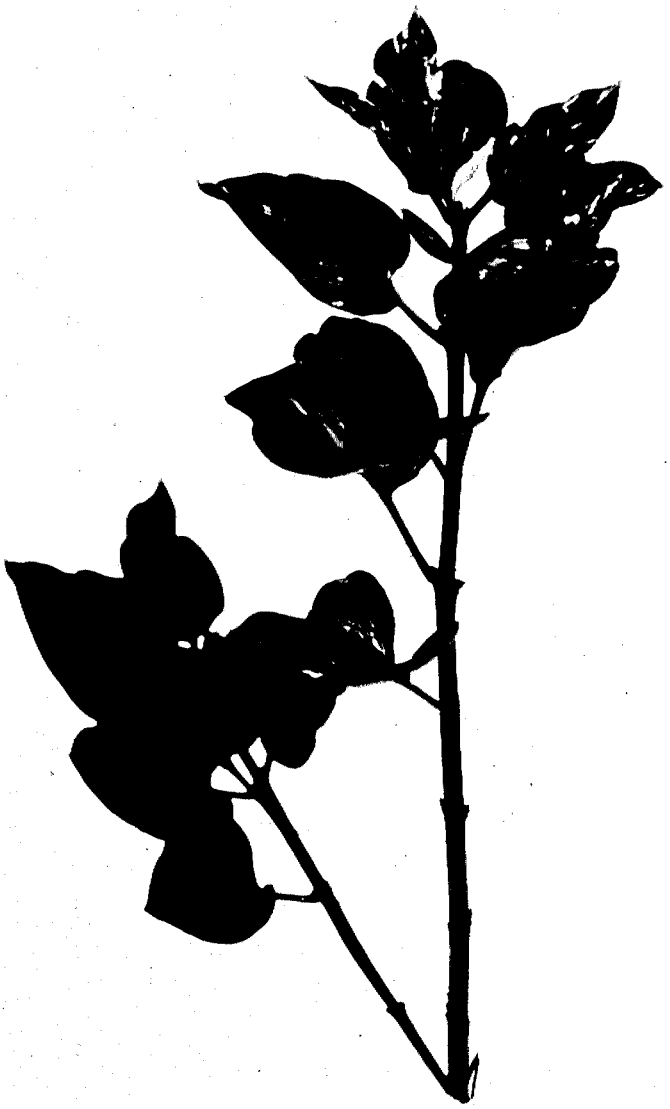
INVENTOR.
CORNELIUS J. HAUCK
BY Pearce & Schaeperklaus
Attorneys United States Patent Office Plant Pat. 2,614
Patented Mar. 22, 1966

2,614
LILAC PLANT

Cornelius J. Hauck, 2625 Reading Road,
Cincinnati, Ohio

Filed Nov. 8, 1962, Ser. No. 236,465
1 Claim. (Cl. Plt.—66)

The present invention or discovery relates to a new and distinct variety of lilac plant.

A common lilac plant, botanically known as *Syringa vulgaris,* not known by me to be patented or otherwise named, is and has been growing in my cultivated garden, which is under my control and supervision and located upon the grounds of my residence in Cincinnati, Hamilton County, Ohio, since I planted it there many years ago. My new variety of *Syringa vulgaris* originated as a bud variation or bud mutation of the above mentioned common lilac plant.

The principal novel characteristics of my new variety by which it is definitely distinguished from the common lilac plant referred to above and from all other varieties of the common lilac, *Syringa vulgaris,* are as follows:

(1) The upper surface of the leaves is semi-glossy and has a dark rich green color, varyingly mottled with irregular areas of whitish, creamy, yellowish and lighter green colors. The coloring of the upper surface of the leaf, particularly the greens, darkens as the leaf ages over a period of many weeks and is quite noticeable through comparison of the newer leaves on mid-season shoots, with mature leaves growing on the plant since the beginning of the season; in some specimens a pink blush which fades away during leaf growth, has been noted in early leaf development stages;

(2) The under surface of the leaves is of a lighter green color than the dark rich green of the upper surface, has a silvery cast and is of rougher, flatter, less glossy appearance than that of the upper surface. The variegated coloration is very subdued, virtually absent from the underside, except when the leaf is viewed from below with strong sunlight striking the upper surface;

(3) The leaves vary in shape or general outline, some being cordate, while others are modified-cordate in which the margins of the leaves have one or more of the following character qualities, repand, irregularly dipped edge, one or more rounded notches in the edge, as appears from the accompanying illustrative drawing; and, (4) The leaves of midseason and later shoots appear to have more resistance to mildew than older leaves on the plant as the leaves on midseason and later shoots remain for a substantial period, free of the whitish powdery mildew so common on lilac leaves in the late summer and in the fall. This freedom from mildew has been particularly noticeable during periods of several weeks duration, during which periods the upper surfaces of older leaves on adjacent portions of the same plant are more or less covered with the whitish mildew.

The plant appears to be substantially identical with its parent in other respects, namely, is an upright early blooming shrub.

Asexual reproduction of my new variety by layering as performed in my garden at Cincinnati, Ohio, shows that the foregoing novel and distinguishing characteristics come true to form and are established and transmitted through subsequent propagation.

The accompanying drawing shows a typical new shoot of my new variety, bearing leaves over two months old, depicted in color as nearly true to life as it is reasonably possible to make the same in a color illustration of this character.

The following is a detailed description of my new variety as observed in my garden at Cincinnati, Ohio, with color terminology in accordance with "A Dictionary of Color by Maerz and Paul," expressed in terms of "plate number—column number—row number," and otherwise in obviously general color terms of ordinary significance, color comparisons being made near midday in open shade on a bright sunny day, under a cloudless sky:

Parentage: Bud variation, sometimes called a bud mutation, of common lilac plant, *Syringa vulgaris.*

Propagation: By layering.

Locality where discovered, propagated, grown and observed: Cincinnati, Hamilton County, Ohio.

Foliage:

Leaf—

*Size.*—Up to 4½ inches wide by 4¼ inches long have been measured on the plant.

*Form, shape or general outline.*—Cordate and modified cordate, in which latter form the margin is repand or irregularly dipped or roundedly notched or has a character which is a combination of one or more of such margin types. New leaves are somewhat cupped or upwardly concave, and as the leaves age, they flatten, some gradually developing some reflexed character.

*Upper surface.*—Smooth with veins slightly indented, semi-glossy; color: green comparable to 23–L–8, 23–E–6, 24–L–6, 24–E–4, mottled with areas of whitish, creamy, yellowish and lighter green colors comparable to 10–E–1, 9–D–1, 19–F–1, 18–H–3, 11–J–1, 12–G–1.

*Underside.*—Slight roughness in appearance with veins slightly projecting from the surface; color: flat green comparable to 23–J–2, 23–J–3, but with a silvery cast.

*Petiole.*—Smooth; color comparable to 20–L–3.

*Buds.*—Elements have a color comparable to 21–K–7, shading toward edge comparable in color to 21–L–1.

*Resistance to mildew.*—New leaves on midseason and later shoots appear to remain free of mildew for a period of weeks, while adjacent old leaves on the plant are covered with mildew.

Wood: New wood has bark of a greenish-brown color comparable to 15–L–9. Old wood has bark of a gray color comparable to 14–A–1.

Plant: Appears to be substantially identical with its parent as to form, an upright shrub, and as to bloom; fragrant, panicles of bright purple-mauve florets.

Having thus described my discovery, I claim:

A new and distinct variety of *Syringa vulgaris* plant as described and illustrated, characterized particularly by the variegated coloring of its leaves.

No references cited.

ABRAHAM G. STONE, *Primary Examiner.*

T. GRAHAM CRAVER, *Examiner.*

R. E. BAGWILL, *Assistant Examiner.*